US009410030B2

(12) United States Patent
Joly et al.

(10) Patent No.: US 9,410,030 B2
(45) Date of Patent: Aug. 9, 2016

(54) ADDITION-FRAGMENTATION AGENTS

(71) Applicant: 3M INNOVATIVE PROPERTIES COMPANY, St. Paul, MN (US)

(72) Inventors: Guy D. Joly, Shoreview, MN (US); Ahmed S. Abuelyaman, Woodbury, MN (US); Ann R. Fornof, St. Paul, MN (US); Bradley D. Craig, Lake Elmo, MN (US); Larry R. Krepski, White Bear Lake, MN (US); William H. Moser, Edina, MN (US); Serkan Yurt, St. Paul, MN (US); Joel D. Oxman, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/437,204

(22) PCT Filed: Nov. 4, 2013

(86) PCT No.: PCT/US2013/068207
§ 371 (c)(1),
(2) Date: Apr. 21, 2015

(87) PCT Pub. No.: WO2014/074427
PCT Pub. Date: May 14, 2014

(65) Prior Publication Data

US 2015/0284538 A1 Oct. 8, 2015

Related U.S. Application Data

(60) Provisional application No. 61/725,061, filed on Nov. 12, 2012.

(51) Int. Cl.

| | |
|---|---|
| ***C08K 5/5455*** | (2006.01) |
| ***C08F 230/08*** | (2006.01) |
| ***C09J 4/06*** | (2006.01) |
| ***C07F 7/18*** | (2006.01) |

(52) U.S. Cl.
CPC ............. *C08K 5/5455* (2013.01); *C07F 7/1844* (2013.01); *C07F 7/1892* (2013.01); *C08F 230/08* (2013.01); *C09J 4/06* (2013.01); *C08F 2438/03* (2013.01)

(58) Field of Classification Search
None
See application file for complete search history.

(56) References Cited

U.S. PATENT DOCUMENTS

| | | | |
|---|---|---|---|
| 2,801,185 | A | 7/1957 | Iler |
| 4,503,169 | A | 3/1985 | Randklev |
| 4,522,958 | A | 6/1985 | Das |
| 4,547,323 | A | 10/1985 | Carlson |
| 4,886,861 | A | 12/1989 | Janowicz |
| 5,324,879 | A | 6/1994 | Hawthorne |
| 5,506,279 | A | 4/1996 | Babu |
| 6,376,590 | B2 | 4/2002 | Kolb |
| 6,572,693 | B1 | 6/2003 | Wu |
| 6,586,483 | B2 | 7/2003 | Kolb |
| 6,730,156 | B1 | 5/2004 | Windisch |
| 6,893,731 | B2 | 5/2005 | Kausch |
| 7,090,721 | B2 | 8/2006 | Craig |
| 7,090,722 | B2 | 8/2006 | Budd |
| 7,156,911 | B2 | 1/2007 | Kangas |
| 7,429,422 | B2 | 9/2008 | Davidson |
| 7,649,029 | B2 | 1/2010 | Kolb |
| 7,838,110 | B2 | 11/2010 | Zhu |
| 7,943,680 | B2 | 5/2011 | Bowman |
| 2005/0256223 | A1 | 11/2005 | Kolb |
| 2006/0009574 | A1 * | 1/2006 | Aert .................... C09D 11/107 524/832 |
| 2008/0076848 | A1 | 3/2008 | Jin |
| 2010/0311858 | A1 | 12/2010 | Holmes |
| 2011/0196062 | A1 | 8/2011 | Craig |
| 2012/0208965 | A1 | 8/2012 | Joly |

FOREIGN PATENT DOCUMENTS

| | | |
|---|---|---|
| EP | 2401998 | 1/2012 |
| WO | WO 2009-091551 | 7/2009 |
| WO | WO 2012-112321 | 8/2012 |
| WO | WO 2012-112350 | 8/2012 |
| WO | WO 2013-028397 | 2/2013 |
| WO | WO 2013-028401 | 2/2013 |

OTHER PUBLICATIONS

Adamson, "Aminoalkyl tertiary Carbinols ", Journal of Chemical Society.; 1949, pp. S144-S152.
Enikolopyan, "Catalyzed Chain Transfer to Monomer in Free Radical Polymerization", Journal of Polymer Science, Polymer. Chemistry, 1981, vol. 19, pp. 879-889.
Hutson, "Chain Transfer Activity of w-Unsaturated Methacrylic Oligomers in Polymerizations of Methacrylic Monomers", Macromolecules, 2004, vol. 37, No. 12, pp. 4441-4452.
Kloxin, "Stress Relaxation via Addition-Fragmentation Chain Transfer in a Thiol-ene Photopolymerization ", Macromolecules, 2009, vol. 42, pp. 2551-2556.
Moad, "Radical addition-fragmentation chemistry in polymer synthesis", Polymer, Mar. 3, 2008, vol. 49, No. 5. pp. 1079-1131.
Temel, "Photopolymerization and photophysical properties of amine linked benzophenone photoinitiators for free rradical polymerization", Journal of Photochemistry and Photobiology A: Chemistry, 2011, vol. 219, pp. 26-31.
International Search Report for PCT International Application No. PCT/US2013/068207, mailed on Feb. 13, 2014, 3pgs.

* cited by examiner

*Primary Examiner* — Robert S Loewe
(74) *Attorney, Agent, or Firm* — Kent S. Kokko

(57) ABSTRACT

Addition-fragmentation agents of the formula are disclosed having the following functional groups: 1) a labile addition-fragmentation group that can cleave and reform to relieve strain, 2) at least two surface-binding functional groups that associate with the surface of a substrate.

14 Claims, No Drawings

ADDITION-FRAGMENTATION AGENTS

CROSS REFERENCE TO RELATED APPLICATIONS

This application is a national stage filing under 35 U.S.C. 371 of PCT/US2013/068207, filed Nov. 4, 2013, which claims priority to Provisional Application No. 61/725061, filed Nov. 12, 2012, the disclosure of which is incorporated by reference in its/their entirety herein.

BACKGROUND

The present disclosure provides novel addition-fragmentation agents for use in low-stress polymerizable compositions. Free-radical polymerization is typically accompanied by a reduction in volume as monomers are converted to polymer. The volumetric shrinkage produces stress in the cured composition, leading to a microcracks and deformation. Stress transferred to an interface between the cured composition and a substrate can cause failure in adhesion and can affect the durability of the cured composition.

The addition-fragmentation agents of this disclosure provide stress relief by including labile linkages that can cleave and reform during the polymerization process. Such cleavage may provide a mechanism to allow for network reorganization, relieve polymerization stress, and prevent the development of high stress regions. The instant addition-fragmentation agents may further provide stress relief by delaying the gel point, the point at which the polymerizable composition transitions from a viscous material to an elastic or viscoelastic solid. The longer the polymerizable mixture remains viscous, the more time available during which material flow can act to alleviate stress during the polymerization process.

The addition-fragmentation agents provide novel stress-reducing agents that have application in dental compositions, thin films, hardcoats, composites, adhesives, and other uses subject to stress reduction. In addition, the addition-fragmentation process results in a chain-transfer event that provides novel polymers that may be further functionalized.

SUMMARY

The present disclosure provides addition-fragmentation agents having the following functional groups: 1) a labile addition-fragmentation group that can cleave and reform to relieve strain, and 2) at least two surface-binding functional groups that associates with the surface of a substrate, such as by forming a covalent or ionic bond.

The addition-fragmentation agents may be added to polymerizable monomer mixtures to reduce the polymerization-induced stresses. This disclosure further provides a method of preparing the addition-fragmentation agents of formula I, as further disclosed herein.

This disclosure further provides a curable composition comprising the addition-fragmentation agent and one or more free-radically polymerizable monomers or oligomers, the addition-fragmentation agent providing a reduction in stress of the resultant polymers. The addition-fragmentation agents act as chain-transfer agents via an addition-fragmentation process whereby the addition-fragmentation linkages are labile during polymerization and continuously cleave and reform, providing a reduction in polymerization-based stress.

This disclosure further provides a curable composition that has at least two surface-binding functional groups that would bond to or associate with, a substrate surface. As result, curable compositions of this disclosure are potentially self-bonding or self-priming.

In some embodiments the addition-fragmentation agent per se may serve as a primer whereby the agent is applied to a substrate and binds therewith.

As used herein:

"acryloyl" is used in a generic sense and mean not only derivatives of acrylic acid, but also amine, and alcohol derivatives, respectively;

"(meth)acryloyl" includes both acryloyl and methacryloyl groups; i.e. is inclusive of both esters and amides.

"curable" means that a coatable material can be transformed into a solid, substantially non-flowing material by means of free-radical polymerization, chemical cross linking, radiation crosslinking, or the like.

"alkyl" includes straight-chained, branched, and cycloalkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent, i.e. monvalent alkyl or polyvalent alkylene.

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent, i.e. monovalent heteroalkyl or polyvalent heteroalkylene.

"aryl" is an aromatic group containing 5-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent, i.e. monovalent aryl or polyvalent arylene.

"(hetero)hydrocarbyl" is inclusive of hydrocarbyl alkyl and aryl groups, and heterohydrocarbyl heteroalkyl and heteroaryl groups, the later comprising one or more catenary (in-chain) oxygen heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxyl)ethyl, 3,6-dioxaheptyl, 3,6-dioxahexyl-6-phenyl, in addition to those described for "alkyl", "heteroalkyl", "aryl", and "heteroaryl" supra.

"Binding" in the context of surface-binding functional groups refers to the formation of a covalent or ionic bond between the addition-fragmentation agent and the substrate.

Binding also includes the etching of the substrate by the surface-binding functional groups.

DETAILED DESCRIPTION

The present disclosure provides addition-fragmentation agents having the following functional groups: 1) a labile addition-fragmentation group that that can cleave and reform to relieve strain, and 2) at least two surface-binding organic functional groups.

The addition-fragmentation group can react into the polymeric system in which the labile group can be added to, fragment, and be added to again by a growing polymer chain to reduce the stress on the growing polymer or polymeric network. Such groups may be selected from those described in G. Moad et al., Radical addition—fragmentation chemistry in polymer synthesis, *Polymer*, Vol. 49, No. 5. (3 Mar. 2008), pp, 1079-1131.

In one preferred embodiment, the present disclosure provides addition-fragmentation agents of the formula:

I

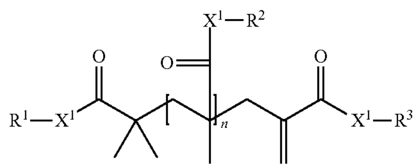

wherein $R^1$, $R^2$ and $R^3$ are each independently $Y_p$-Q'-, a (hetero) alkyl group or a (hetero)aryl group with the proviso that at least two of $R^1$, $R^2$ and $R^3$ is $Y_p$-Q'

- Q' is a covalent bond or a linking group, preferably a (hetero)hydrocarbyl linking group, having a valence of p+1;

Y is a surface-binding functional group;

p is 1 or 2;

each $X^1$ is independently —O— or —$NR^4$—, where $R^4$ is H or $C_1$-$C_4$ alkyl, and n is 0 or 1. It will be further understood that each of $R^1$, $R^2$ and $R^3$ may contain more than one $Y_p$-Q'- group.

With further respect to Formula I, particularly useful Y groups ($R^1$—$X^1$— groups and optionally $R^2$—$X^1$— and $R^3$—$X^1$ groups) include a monophosphate, a phosphonate, a phosphonic acid, a hydroxamic acid, a carboxylic acid, and acetoacetate, an anhydride, an isonitrile group, a silyl, a disulfide, a thiol, an amino, a sulfinic acid, a sulfonic acid, a phosphine, a phenolic (including catechols and 1,2,3-trihydroxy benzene derivatives), or a heterocyclic aromatic group. Of particular interest is Y selected as a silyl group of the formula —$SiR^7_3$, wherein each $R^7$ group is independently selected from the group of alkoxy, acetoxy, and halide.

It is believed that the addition-fragmentation agent follows an addition-fragmentation pathway as shown in the following Scheme 1. In this scheme the addition-fragmentation group/agent of Formula I is shown, where n is 0. In the step 1, a free radical species P. adds to the addition-fragmentation agent. The addition-fragmentation agent then fragments as shown in step 2 to form the stable α-carbonyl tertiary radical and the α,β-unsaturated ester bearing the residue of the free radical species P. This α,β-unsaturated ester can undergo radical addition as shown in step 5. The radical addition may be initiated by an initiator or a polymer radical.

Concurrently the α-carbonyl tertiary radical can initiate polymerization of monomer as shown in step 3. For purposes of illustration, a methacrylate monomer is illustrated. On monomer addition, a methacrylate-terminated radical intermediate is produced. In the presence of the addition-fragmentation agent of Formula 1 (as shown in step 4) both addition and fragmentation, yielding a tertiary radical, occurs. The polymer resulting from step 4 may further fragment and recombine or add additional monomer(s).

Scheme 1.

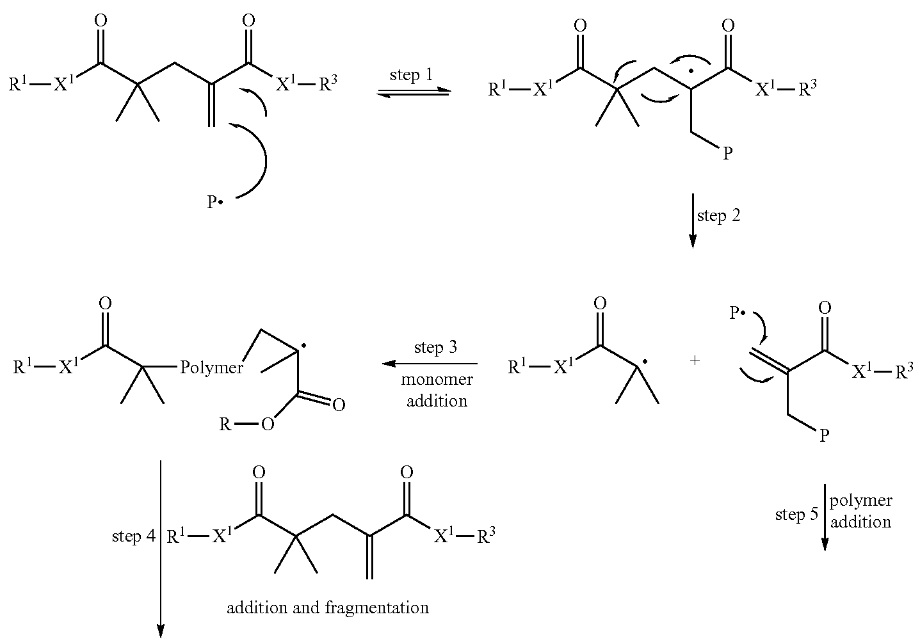

-continued

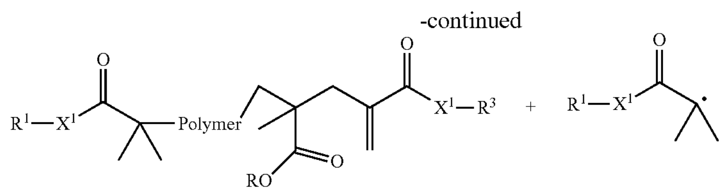

Stress relief could also be a result of attenuated reaction rates (slower cure rates) in the presence of addition-fragmentation agents. The addition of a radical to the addition-fragmentation agent generates a potentially long-lived, tertiary radical (the product of step 1, Scheme 1). This long-lived radical intermediate can revert back to starting materials, add to monomer, or fragment. If fragmentation, retro-addition and monomer addition are slow relative to addition, the intermediate tertiary radical will be relatively long-lived. This long-lived radical intermediate will then act as a radical reservoir, slowing down the overall polymerization process. Attenuated cure rates could serve to delay the transition of a material from a viscous material to an elastic or viscoelastic solid, delaying the gel point. Post-gel shrinkage is a major component in stress development; therefore, delaying the gel point even slightly may lead to stress relief by allowing additional time for material to flow during the curing process. Therefore, even compounds of Formula I may be used to reduce polymerization stress.

The compounds of Formula I may be prepared from (meth) acrylate dimers and trimers by substitution, displacement or condensation reactions. The starting (meth)acrylate dimers and trimers may be prepared by free radical addition of a (meth)acryloyl monomer in the presence of a free radical initiator and a cobalt (II) complex catalyst using the process of U.S. Pat. No. 4,547,323 (Carlson), incorporated herein by reference. Alternatively, the (meth)acryloyl dimers and trimers may be prepared using a cobalt chelate complex using the processes of U.S. Pat. No. 4,886,861 (Janowicz) or U.S. Pat. No. 5,324,879 (Hawthorne), incorporated herein by reference. In either process, the reaction mixture can contain a complex mixture of dimers, trimers, higher oligomers and polymers and the desired dimer or trimer can be separated from the mixture by distillation.

With reference to Formula I, the requisite "Y" group may be incorporated into the (meth)acryloyl dimer or trimer by means including addition, condensation, substitution and displacement reaction. In general, one or more of the acyl groups of the (meth)acryloyl dimer or trimer is provided with the $Y_p$-Q'-$X^1$— group of Formula I.

More specifically, a (meth)acryloyl compound of the formula:

IIa

IIb

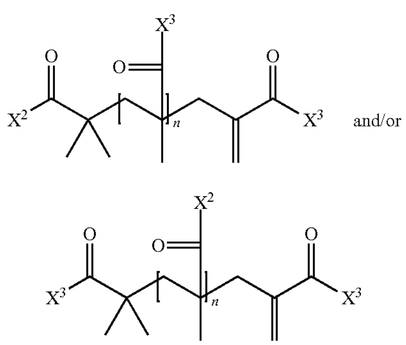

wherein $X^2$ comprises an electrophilic or nucleophilic functional group, $X^3$ is independently $X^2$, $X^1$—$R^2$ or $X^1$—$R^3$, and n is 0 or 1;

is reacted with a co-reactive compound of the formula:

$$A^2\text{-}R^{5*}\text{—}Y \qquad \text{III}$$

wherein $A^2$ is a functional group that is co-reactive with functional group $X^2$, $R^{5*}$ is a single bond or a di- or trivalent (hetero)hydrocarbyl linking group that joins the Y group to reactive functional group $A^2$. As result of the reaction, the addition-fragmentation agents are provided with two or more surface-binding functional groups Y.

In some embodiments a compound of Formula II is reactive with a compound of Formula III, where $A^2$ comprises an epoxy or aziridine functional group. The reaction product has, in addition to the requisite Y group, a hydroxyl group or amine group that may be further functionalized with additional surface-binding functional groups Y, or non-reactive groups such as alkyl or aryl groups.

More specifically, $R^{5*}$ is a single bond or a di- or trivalent linking group that joins an surface-binding group to co-reactive functional group $A^2$ and preferably contains up to 34, preferably up to 18, more preferably up to 10, carbon and, optionally, oxygen and nitrogen atoms, optional catenary ester, amide, urea, urethane and carbonate groups. When $R^{5*}$ is not a single bond, is may be selected from —O—, —S—, —N—$R^4$—, —$SO_2$—, —$PO_2$—, —CO—, —OCO—, —N($R^4$)—CO—, —N($R^4$)—CO—O—, —N($R^4$)—CO—N($R^4$)—, —$R^6$— and combinations thereof, such as —CO—O—$R^6$—, —CO—N($R^4$)—$R^6$—, and —$R^6$—CO—O—$R^6$—.

wherein each $R^4$ is hydrogen, a $C_1$ to $C_4$ alkyl group, or aryl group, each $R^6$ is an alkylene group having 1 to 6 carbon atoms, a 5- or 6-membered cycloalkylene group having 5 to 10 carbon atoms, or a divalent aromatic group having 6 to 16 carbon atoms.

It will be understood that reaction between the $X^2$ group of Formula II and the $A^2$ group of Formula III will form the $Y_p$-Q'-$X^1$— moiety of Formula I, therefore Q' may be defined as —$R^5$-$A^{2*}$—$X^{2*}$—, where $A^{2*}$—$X^{2*}$- is the bond formed between $A^2$ and $X^2$, as described supra. Therefore Q' may be defined as single bond or a divalent linking (hetero)hydrocarbyl group. More particularly, Q' a single bond or a divalent linking group that joins a surface-binding group to co-reactive functional group A and preferably contains up to 34, preferably up to 18, more preferably up to 10, carbon and, optionally, oxygen and nitrogen atoms, optional catenary ester, amide, urea, urethane and carbonate groups. When Q is not a single bond, it may be selected from —O—, —S—, —$NR^4$—, —$SO_2$—, —$PO_2$—, —CO—, —OCO—, —$R^6$— and combinations thereof, such as —N($R^4$)—CO—O—, —N($R^4$)—CO—N($R^4$)—, —CO—O—$R^6$—, —CO—$NR^4$—$R^6$—, and —$R^6$—CO—O—$R^6$—, —O—$R^6$—. —S—$R^6$—, —N($R^4$)—$R^6$—, —$SO_2$—$R^6$—, —$PO_2$—

$R^6$—, —CO—$R^6$—, —OCO—$R^6$—, —N($R^4$)—CO—$R^6$—, $NR^4$—$R^6$—CO—O—, N($R^4$)—CO—N($R^4$)—, —$R^6$—, with the proviso that Q'-$Y_p$ does not contain peroxidic linkages, i.e. O—O, N—O, S—O, N—N, N—S bonds, wherein each $R^4$ is hydrogen, a $C_1$ to $C_4$ alkyl group, or aryl group, each $R^6$ is an alkylene group having 1 to 6 carbon atoms, a 5- or 6-membered cycloalkylene group having 5 to 10 carbon atoms, or a divalent arylene group having 6 to 16 carbon atoms.

In some embodiments the compound of Formula II is reacted with an aziridine- or epoxy-functional compound as illustrated in Scheme III. It will be understood that different isomers from those depicted may result from the ring-opening. In Scheme III, transverse methyl groups are indicated as attached to either of the adjacent carbon atoms. The illustrated products, having an amine or hydroxyl groups respectively, may then be provided with the surface-binding functional group by reaction with a compound of the formula IIb: $A^2$-$R^{5*}$—Y. For example, the illustrated products may be provided with silyl surface-binding groups by reaction with a silylalkylisocyanate.

Scheme III

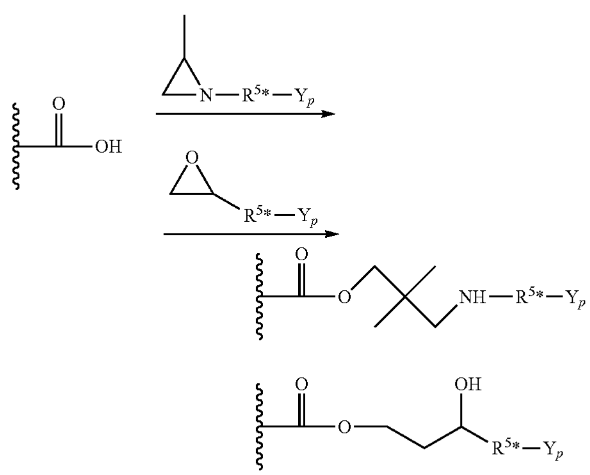

Alternatively, a compound of Formula II is reacted with an aziridine- or epoxy-functional compound to form an intermediate functional group as illustrated in Scheme IV. In the reaction scheme the product is further functionalized to provide the requisite surface binding groups Y. Alternatively, an epoxy- or aziridine-functional polymer can be further functionalized with a nucleophilic compound of Formulas IIIa or b to produce the compounds of Formula I. For example, the acid group shown may be reacted with an epoxy compounds, then the hydroxy group resulting from ring-opening may be reacted with an isocyanatoalkyl trialkoxy silane to provide silane surface-binding functional groups.

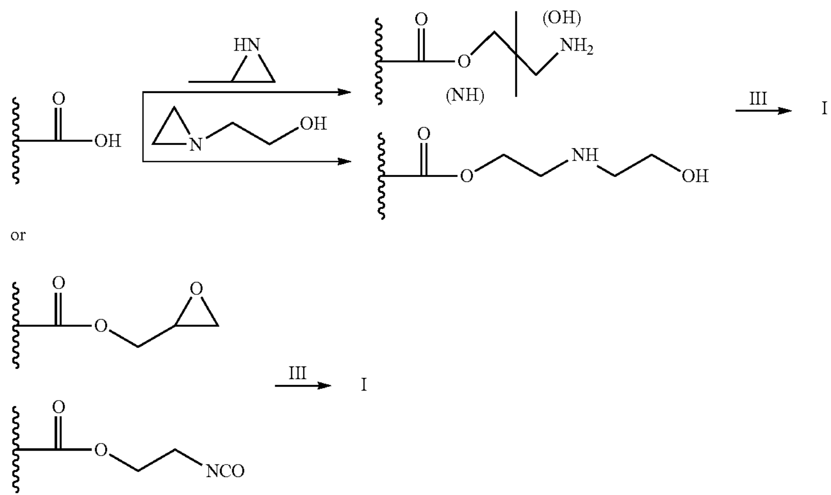

Useful reactive (and co-reactive) functional groups ($X^2$ and A2 of Formula III) include hydroxyl, secondary amino, oxazolinyl, oxazolonyl, acetylacetonate, carboxyl, isocyanato, epoxy, aziridinyl, acyl halide, and cyclic anhydride groups. Where the reactive functional group of the (meth) acrylate dimer/trimer is an isocyanato functional group, the co-reactive functional group preferably comprises a primary or secondary amino or hydroxyl group. Where the reactive functional group comprises a hydroxyl group, the co-reactive functional group preferably comprises a carboxyl, ester, acyl halide, isocyanato, epoxy, anhydride, or oxazolinyl group. Where the pendent reactive functional group comprises a carboxyl group, the co-reactive functional group preferably comprises a hydroxyl, amino, epoxy, isocyanate, or oxazolinyl group. Most generally, the reaction is between a nucleophilic and electrophilic functional groups.

With respect to Formula III, the reactive group $A^2$ may be selected from those described supra. Y is a surface-binding group that interacts with a substrate (e.g., the backing of a tape, metal surface, glass, glass cloth, or any surface to which the Y group displays an affinity) on which the curable composition is disposed (i.e., interacting physically or chemically, which can be covalent or ionic, for example), or on a filler surface In some embodiments Y is a thiol group (—SH), a monophosphate group, a phosphonate or phosphonic acid group (—P(O)$(OH)_2$), a hydroxamic acid group (—C(O)NHOH), a carboxylic acid group (—C(O)OH), a sulfinic or sulfonic acid group, a phospine group, phenolic groups (including catechols and 1,2,3-trihydroxy benzene derivatives), amines, an isonitrile group, a silyl group, a disulfide group (—S—S—). or a heterocyclic aromatic group (e.g., benzotriazolyl, thiazoyl, benzimidaolyl or pyridinyl).

More preferably, Y is a thiol group, a monophosphate group, a phosphonate group, a carboxylic acid group, a silyl group, or a benzotriazole group. For aluminum oxide substrates, preferably Y includes a phosphonic acid group (—P(O)(OH)$_2$), a hydroxamic acid group (—C(O)NHOH), or a carboxylic acid group (—C(O)OH). For iron oxide or steel substrates, preferably Y includes a hydroxamic acid group (—C(O)NHOH). For copper oxide, preferably Y includes a hydroxamic acid group (—C(O)NHOH), a thiol group (—SH), a monophosphate group, a phosphonate or phosphonic acid group, a triazolyl group, a thiazolyl group, a benzimidazolyl group, or a pyridinyl group. For silicon oxide or glass, preferably Y is a silyl group of the formula —SiR$^7_3$, wherein each R$^7$ group is independently selected from the group of alkoxy, acetoxy, and halide. For gold, copper, and silver, preferably Y is a thiol group (—SH) or a disulfide group (—S—S—). For platinum, preferably Y includes a pyridinyl or a phosphine group.

It will also be understood that the compounds of Formula II may be provided with other nucleophilic or electrophilic functional groups, in addition to simple esters or amides. With reference to the X$^2$ group of Formula II, which comprises an electrophilic or nucleophilic functional groups, X$^2$ may be selected from —OH, —Cl, —Br, —NR$^4$H, —R$^6$—NCO, —R$^6$—SH, —R$^6$—OH, —R$^6$—NR$^4$H, —R$^6$—Si(OR$^4$)$_3$, —R$^6$-halide, —R$^6$-aziridine, —R$^6$-epoxy, —R$^6$—N$_3$, —R$^6$-anhydride, —R$^6$-succinate, —R$^6$—NR$^4$H, and other electrophilic or nucleophilic functional groups.

wherein each R$^6$ is an alkylene group having 1 to 6 carbon atoms, a 5- or 6-membered cycloalkylene group having 5 to 10 carbon atoms, or a divalent aromatic group having 6 to 16 carbon atoms. R$^6$ may be substituted with one or more in-chain functional groups, including ether, amine, thioether, ester, amide, urea, and urethane functional groups, for example R$^6$—NH—CO—O—R$^{6'}$—NCO, where R$^{6'}$ is defined as R$^6$. R$^4$ is H or C$_1$-C$_4$ alkyl.

The present disclosure further provides a polymerizable composition comprising the addition-fragmentation agent of Formula I, and at least one polymerizable monomer, such as (meth)acryloyl monomers, including acrylate esters, amides, and acids to produce (meth)acrylate homo- and copolymers. Generally, the addition-fragmentation agent of Formula I is used in amounts of 0.1 to 12 parts by weight, preferably 0.1 to 8 parts by weight, based on 100 parts by weight of total monomer.

The (meth)acrylate ester monomer useful in preparing the (meth)acrylate polymer is a monomeric (meth)acrylic ester of a non-tertiary alcohol, which alcohol contains from 1 to 14 carbon atoms and preferably an average of from 4 to 12 carbon atoms.

Examples of monomers suitable for use as the (meth)acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomer are suitable. In some embodiments, the preferred (meth)acrylate ester monomer is the ester of (meth)acrylic acid with an alcohol derived from a renewable source, such as 2-octanol, citronellol, dihydrocitronellol.

In some embodiments it is desirable for the (meth)acrylic acid ester monomer to include a high $T_g$ monomer, having a $T_g$ of at least 25° C., and preferably at least 50° C. Examples of suitable monomers useful in the present invention include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, tetrahydrofurfuryl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, and propyl methacrylate or combinations.

The (meth)acrylate ester monomer is present in an amount of up to 100 parts by weight, preferably 85 to 99.5 parts by weight based on 100 parts total monomer content used to prepare the polymer. Preferably (meth)acrylate ester monomer is present in an amount of 90 to 95 parts by weight based on 100 parts total monomer content. When high $T_g$ monomers are included in some embodiments, the copolymer may include up to 30 parts by weight, preferably up to 20 parts by weight of the (meth)acrylate ester monomer component. In other embodiments, for example structural adhesives, the high $T_g$ monomers may comprises up to 100% if the (meth) acrylate ester monomer component The polymer may further comprise an acid functional monomer, where the acid functional group may be an acid per se, such as a carboxylic acid, or a portion may be salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, acid functional monomers of the acid functional copolymer are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids. The acid functional monomer is generally used in amounts of 0.5 to 15 parts by weight, preferably 1 to 15 parts by weight, most preferably 5 to 10 parts by weight, based on 100 parts by weight total monomer.

The polymer may further comprise a polar monomer. The polar monomers useful in preparing the copolymer are both somewhat oil soluble and water soluble, resulting in a distribution of the polar monomer between the aqueous and oil phases in an emulsion polymerization. As used herein the term "polar monomers" are exclusive of acid functional monomers.

Representative examples of suitable polar monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; poly(alkoxyalkyl) (meth)acrylates including 2-(2-ethoxyethoxyl)ethyl (meth)acrylate, 2-ethoxyethyl (meth)acrylate, 2-methoxyethoxyethyl (meth)acrylate, 2-methoxyethyl methacrylate, polyethylene glycol mono(meth)acrylates;

alkyl vinyl ethers, including vinyl methyl ether; and mixtures thereof. Preferred polar monomers include those selected from the group consisting of 2-hydroxyethyl (meth)acrylate and N-vinylpyrrolidinone. The polar monomer may be present in amounts of 0 to 10 parts by weight, preferably 0.5 to 5 parts by weight, based on 100 parts by weight total monomer.

The polymer may further comprise a vinyl monomer. When used, vinyl monomers useful in the (meth)acrylate polymer include vinyl esters (e.g., vinyl acetate and vinyl propionate), styrene, substituted styrene (e.g., α-methyl styrene), vinyl halide, and mixtures thereof. As used herein vinyl monomers are exclusive of acid functional monomers, acrylate ester monomers and polar monomers. Such vinyl monomers are generally used at 0 to 5 parts by weight, preferably 1 to 5 parts by weight, based on 100 parts by weight total monomer.

In order to increase the cohesive strength of the composition, a multifunctional (meth)acrylate may be incorporated into the blend of polymerizable monomers. Multifunctional acrylates are particularly useful for emulsion or syrup polymerization. Examples of useful multifunctional (meth)acrylates include, but are not limited to, di(meth)acrylates, tri (meth)acrylates, and tetra(meth)acrylates, such as 1,6-hexanediol di(meth)acrylate, poly(ethylene glycol) di(meth) acrylates, polybutadiene di(meth)acrylate, polyurethane di(meth)acrylates, and propoxylated glycerin tri(meth)acrylate, and mixtures thereof. The amount and identity of multifunctional (meth)acrylate is tailored depending upon application of the adhesive composition. Typically, the multifunctional (meth)acrylate is present in amounts less than 5 parts based on total dry weight of adhesive composition. More specifically, the crosslinker may be present in amounts from 0.01 to 5 parts, preferably 0.05 to 1 parts, based on 100 parts total monomers of the adhesive composition.

In such embodiments, the copolymer may comprise:

i. up to 100 parts by weight, preferably 85 to 99.5 parts by weight of an (meth)acrylic acid ester;
ii. 0 to 15 parts by weight, preferably 0.5 to 15 parts by weight of an acid functional ethylenically unsaturated monomer;
iii. 0 to 15 parts by weight of a non-acid functional, ethylenically unsaturated polar monomer;
iv. 0 to 5 parts vinyl monomer;
v. 0 to 5 parts of a multifunctional (meth)acrylate;
vi. 0 to 5 parts of a photoinitiator. based on 100 parts by weight total monomer.

The composition may be polymerized with either a thermal initiator or photoinitiator. Any free radical initiator may be used to generate the initial radical. Examples of suitable thermal initiators include peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2,-azo-bis(isobutyronitrile), and t-butyl perbenzoate. Examples of commercially available thermal initiators include initiators available from DuPont Specialty Chemical (Wilmington, Del.) under the VAZO trade designation including VAZO™ 67 (2,2'-azo-bis(2-methybutyronitrile)) VAZO™ 64 (2,2'-azo-bis(isobutyronitrile)) and VAZO™ 52 (2,2'-azo-bis(2,2-dimethyvaleronitrile)), and Lucidol™ 70 from Elf Atochem North America, Philadelphia, Pa.

Useful photoinitiators include benzoin ethers such as benzoin methyl ether and benzoin isopropyl ether; substituted acetophenones such as 2,2-dimethoxyacetophenone, available as Irgacure™ 651 photoinitiator (Ciba Specialty Chemicals), 2,2 dimethoxy-2-phenyl-1-phenylethanone, available as Esacure™ KB-1 photoinitiator (Sartomer Co.; West Chester, Pa.), and dimethoxyhydroxyacetophenone; substituted α-ketols such as 2-methyl-2-hydroxy propiophenone; aromatic sulfonyl chlorides such as 2-naphthalene-sulfonyl chloride; and photoactive oximes such as 1-phenyl-1,2-propanedione-2-(O-ethoxy-carbonyl)oxime. Particularly preferred among these are the substituted acetophenones.

The photoinitiator may also be a polymerizable photoinitiator having a free-radically polymerizable groups and a photoinitiator group. Such polymerizable photoinitiators include 4-benzoylpenyl acrylate, 2-(4-benzoylphenoxyl) ethyl acrylate and 2-[4-(2-hydroxy-2-methylpropanoyl)phenoxy]ethyl-N-acryloyl-2-methylalinate, and are described in U.S. Pat. No. 7,838,110 (Zhu et al.), U.S. Pat. No. 5,506,279 (Babu et al.), incorporated herein by reference, and also Temel et al. "Photopolymerization and photophysical properties of amine linked benzophenone photoinitiators for free radical polymerization", Journal of Photochemistry and Photobiology A, Chemistry 219 (2011), pp. 26-31.

The initiator is used in an amount effective to facilitate free radical addition to the addition-fragmentation crosslinking agent and the amount will vary depending upon, e.g., the type of initiator and the molecular weight of the polymer and the degree of functionalization desired. The initiators can be used in amounts from about 0.001 part by weight to about 5 parts by weight based on 100 parts total monomer.

The curable composition may also include other additives. Examples of suitable additives include tackifiers (e.g., rosin esters, terpenes, phenols, and aliphatic, aromatic, or mixtures of aliphatic and aromatic synthetic hydrocarbon resins), surfactants, plasticizers (other than physical blowing agents), nucleating agents (e.g., talc, silica, or $TiO_2$), pigments, dyes, reinforcing agents, solid fillers, rubber tougheners, stabilizers (e.g., UV stabilizers), and combinations thereof. The additives may be added in amounts sufficient to obtain the desired properties for the cured composition being produced. The desired properties are largely dictated by the intended application of the resultant polymeric article.

In some embodiments the crosslinkable composition may include filler. In some embodiments the total amount of filler is at most 50 wt. %, preferably at most 30 wt. %, and more preferably at most 10 wt. % filler. Fillers may be selected from one or more of a wide variety of materials, as known in the art, and include organic and inorganic filler. Inorganic filler particles include silica, submicron silica, zirconia, submicron zirconia, and non-vitreous microparticles of the type described in U.S. Pat. No. 4,503,169 (Randklev).

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911 (Kangas et al.), and U.S. Pat. No. 7,649,029 (Kolb et al.).

In some preferred embodiments, the curable composition comprises nanoparticles and/or nanoclusters surface treated with an organometallic coupling agent to enhance the bond between the filler and the monomers/and/or polymers. The organometallic coupling agent may be functionalized with reactive curing groups, such as acrylates, methacrylates, vinyl groups and the like and may comprise silane, zirconate or titanate coupling agents. Suitable copolymerizable or reactive organometallic compounds may have the general formulas: $CH_2{=}C(R^{22}){-}R^{21}Si(OR)_nR_{3-n}$ or $CH_2{=}C(R^{22}){-}C{=}OOR^{21}Si(OR)_nR_{3-n}$; wherein R is an $C_1$-$C_4$ alkyl, $R^{21}$ is a divalent organic heterohydrocarbyl linking group, preferably alkylene; $R^{22}$ is H or C1-C4 alkyl; and n is from 1 to 3.

Preferred coupling agents include gamma-methacryloxypropyltrimethoxysilane, gamma-mercaptopropyltriethoxysilane, gamma-aminopropyltrimethoxysilane, and the like.

A variety of conventional methods are available for modifying the surface of nanoparticles including, e.g., adding a surface-modifying agent to nanoparticles (e.g., in the form of a powder or a colloidal dispersion) and allowing the surface-modifying agent to react with the nanoparticles. Other useful surface-modification processes are described in, e.g., U.S. Pat. No. 2,801,185 (Iler), U.S. Pat. No. 4,522,958 (Das et al.) U.S. Pat. No. 6,586,483 (Kolb et al.), each incorporated herein by reference.

Surface-modifying groups may be derived from surface-modifying agents. Schematically, surface-modifying agents can be represented by the formula A-B, where the A group is capable of attaching to the surface of the particle (i.e., the silanol groups of a silica particle) and the B group is a reactive or non-reactive functional group. A non-reactive group is one that does not react with other components in the system (e.g. the substrate). Non-reactive functional groups can be selected to render the particle relatively more polar, relatively less polar or relatively non-polar. In some embodiments the non-reactive functional group "B" is a hydrophilic group such as an acid group (including carboxylate, sulfonate and phosphonate groups), ammonium group or poly(oxyethylene) group, or hydroxyl group. In other embodiments, "B" may be a reactive functional groups such as an ethylenically unsaturated polymerizable group, including vinyl, allyl, vinyloxy, allyloxy, and (meth)acryloyl, that may be free-radically polymerized with the polymerizable resin or monomers.

Such optional surface-modifying agents may be used in amounts such that 0 to 100%, generally 1 to 90% (if present) of the surface functional groups (Si—OH groups) of the silica nanoparticles are functionalized. The number of functional groups is experimentally determined where quantities of nanoparticles are reacted with an excess of surface modifying agent so that all available reactive sites are functionalized with a surface modifying agent. Lower percentages of functionalization may then be calculated from the result. Generally, the amount of surface modifying agent is used in amount sufficient to provide up to twice the equal weight of surface modifying agent relative to the weight of inorganic nanoparticles. The amount of surface modifying agents will vary by the specific filler, size thereof and desired degree of functionalization. If surface-modified silica nanoparticles are desired, it is preferred to modify the nanoparticles prior to incorporation into the coating composition.

In some preferred embodiments, the fillers, particularly the silica fillers, may be surface modified with the addition-fragmentation agent of Formula I. Thus the present disclosure provides addition-fragmentation monomer-modified filler particles. These surface modified filler particles may be compounded with the polymerizable mixture and cured as described herein, with the result that the filler particles are integrated into the cured composition. With reference to Formula I, the surface-modified particle filler may be illustrated as:

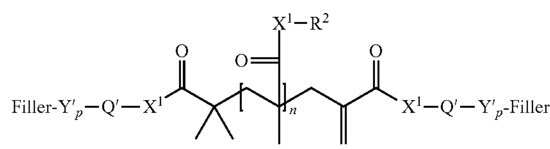

where

Filler is an inorganic filler particle, $R^2$ is $Y_p$-Q'—, a (hetero)alkyl group or a (hetero)aryl group;

Q' is a covalent bond or an or a linking group, preferably an organic (hetero)hydrocarbyl linking group having a valence of p+1;

Y' is the residue of the surface-binding organic functional group that associates with a substrate on which the addition-fragmentation agent is disposed;

p is 1 or 2;

$X^1$ is independently —O— or —$NR^4$—, where $R^4$ is H or $C_1$-$C_4$ alkyl, and n is 0 or 1.

It will be understood in the above Formula that the $R^1$ and $R^3$ groups of formula I were chosen with the "Y-Q'-" surface binding group and that $R^2$ could be so illustrated. It will be further understood that each of $R^1$, $R^2$ and $R^3$ may contain a $Y_p$-Q'- group and that each can contain one or more Y groups.

As used herein the term "residue" is used to define that portion of a functional group remaining after reaction of the functional group with the surface of the inorganic particulate For example, the "residue" of a silane functional group Y of the formula —$SiR^7_3$, would be —O—$Si(R^7)_2$—.

For further illustration, the particular filler may be selected from silica (or a silica composite), and the surface-binding organic functional group "Y" may be selected from a silyl group of the formula —$SiR^7_3$, wherein each $R^7$ group is independently selected from the group of alkoxy, acetoxy, and halide. This would result in a covalent bond between the silica particle and the addition-fragmentation agent illustrated by a Silica-O—$Si(R^7)_2$-linkage. It will be understood that the silyl moiety may form one (as illustrated) or more siloxane bonds with a silica particle or siloxane bonds with other silyl groups. With reference to formula I, one may select Y=hydroxamic acid or N-hydroxyurea that may bond to zirconia, a filler used in high index coatings/films as well as in dental composites, Y=phosphates and phosphonates would also be useful for alumina fillers, and Y=thiols for gold.

In general, all or a part of the surface functional groups of an inorganic filler particle may be so modified by the addition-fragmentation agent of Formula I. The fillers may be unmodified, surface modified by conventional surface-modifying agents, the addition-fragmentation agents of Formula I, or a mixture of conventional surface-modifying agents and those of Formula I. Preferably, the addition-fragmentation agent is used in amounts of 0.5 to 30 wt. %, relative to the weight of the filler particles. In particular, higher amounts of nanoparticles may be used relative to larger sized filler particles e.g. >100 nm.

The surface modification can be done either subsequent to mixing with the polymerizable monomers during or after mixing. It is typically preferred to combine the organosilane surface treatment compounds with nanoparticles before incorporation into the resin. The required amount of surface modifier is dependent upon several factors such as particle size, particle type, modifier molecular weight, and modifier type. In general it is preferred that approximately a monolayer of modifier is attached to the surface of the particle.

The present addition fragmentation agents are also useful in the preparation of hardcoats. The term "hardcoat" or "hardcoat layer" means a layer or coating that is located on the external surface of an object, where the layer or coating has been designed to at least protect the object from abrasion. The present disclosure provides hardcoat compositions comprising the addition-fragmentation agent of Formula I and, a multi-functional (meth)acrylate monomer comprising three or more (meth)acrylate groups, and/or a multi- functional (meth)acrylate oligomer and optionally a (meth)acrylate-functional diluent.

Useful multifunctional (meth)acrylate monomers comprise three or more (meth)acrylate groups. Multifunctional (meth)acrylate monomers are useful in the practice of the present invention because they add abrasion resistance to the hardcoat layer. Preferred multifunctional (meth)acrylate monomers comprising three or more (meth)acrylate groups include trimethylol propane tri(meth)acrylate (TMPTA), pentaerythritol tri(meth)acrylate, pentaerythritol tetra(meth) acrylate, ditrimethylolpropane tri(meth)acrylate (Sartomer 355), dipentaerythritol penta(meth)acrylate (Sartomer 399), dipentaerythritol hydroxy penta(meth)acrylate (DPHPA), glyceryl propoxy tri(meth)acrylate, trimethylolpropane tri (meth)acrylate, and mixtures thereof. Another useful radiation-curable component of the present invention is the class of multifunctional (meth)acrylate oligomers, having two or more (meth)acrylate groups, and having an average molecular weight (Mw) in the range from about 400 to 2000.

Useful multi-functional (meth)acrylate oligomers include polyester (meth)acrylates, polyurethane (meth)acrylates, and (meth)acrylated epoxy (meth)acrylates. (Meth)acrylated epoxy (meth)acrylates and polyester(meth)acrylates are most preferred because they tend to have a relatively low viscosity and therefore allow a more uniform layer to be applied by the spin coating method. Specifically, preferred multifunctional (meth)acrylate oligomers include those commercially available from UCB Radcure, Inc. of Smyrna, Ga. and sold under the trade name Ebecryl (Eb): Eb40 (tetrafunctional acrylated polyester oligomer), ENO (polyester tetra-functional (meth) acrylate oligomer), Eb81 (multifunctional (meth)acrylated polyester oligomer), Eb600 (bisphenol A epoxy di(meth) acrylate), Eb605 (bisphenol A epoxy di(meth)acrylate diluted with 25% tripropylene glycol di(meth)acrylate), Eb639 (novolac polyester oligomer), Eb2047 (trifunctional acrylated polyester oligomer), Eb3500 (di- functional Bisphenol-A oligomer acrylate), Eb3604 (multi-functional polyester oligomer acrylate), Eb6602 (trifunctional aromatic urethane acrylate oligomer), Eb8301 (hexafunctional aliphatic urethane acrylate), EbW2 (difunctional aliphatic urethane acrylate oligomer), and mixtures thereof. Of these, the most preferred are, Eb 600, Eb605, Eb80, and Eb81.

The (meth)acrylate-functional diluents, also referred to herein as "reactive diluents," are relatively low molecular weight mono- or di-functional, (meth)acrylate monomers. These relatively low molecular weight reactive diluents are advantageously of a relatively low viscosity, e.g., less than about 30 centipoise (cps) at 25° C. Di-functional, non-aromatic (meth)acrylates are generally preferred over monofunctional non-aromatic (meth)acrylates because di-functional non-aromatic (meth)acrylates allow for quicker cure time. Preferred reactive diluents include 1,6-hexanediol di(meth)acrylate (HDDA from UCB Radcure, Inc. of Smyrna, Ga.), tripropylene glycol di(meth)acrylate, isobornyl (meth)acrylate (1130A, Radcure), 2(2-ethoxyethoxy) ethyl (meth)acrylate (sold under the trade name Sartomer 256 from SARTOMER Company, Inc. of Exton, Pa.), n-vinyl formamide (Sartomer 497), tetrahydrofurfuryl (meth) acrylate (Sartomer 285), polyethylene glycol di(meth)acrylate (Sartomer 344), tripropylene glycol di(meth)acrylate (Radcure), neopentyl glycol dialkoxy di(meth)acrylate, polyethyleneglycol di(meth)acrylate, and mixtures thereof.

The hardcoat composition may comprise:

0.1-12 wt. % of the addition-fragmentation (AFM) and/or AFM-modified silica, the weight percents referring to the AFM per se, whether as a functionalized filler or not (0.1-12 wt. % AFM)

20-75 wt. % of multifunctional (meth)acrylate monomers and/or multifunctional (meth)acrylate oligomers, 0 to 25 wt. % range of (meth)acrylate diluent, (0-25 wt. %)

20 to 75 wt. % of an inorganic filler such as silica, the weight ranges referring to the inorganic filler per se, whether or not functionalized.

In some embodiments the amount of silica, including the AFM surface modified silica, silica modified with conventional surface modifying agents and unmodified silica is 20-75 wt. %., preferably 50-70 wt. %.

In some embodiments the addition-fragmentation agent per se may serve as a primer whereby the agent is applied to a substrate and binds therewith. In these embodiments a thin layer of the AFM of Formula I may be applied to a substrate and then an additional layer applied to the AFM-primed substrate. The specific binding group Y is chosen as a functional of the selected substrate as taught supra. For example, aluminum oxide substrates, preferably Y includes a phosphonic acid group, a hydroxamic acid group, or a carboxylic acid group. For iron oxide or steel substrates, preferably Y includes a hydroxamic acid group. For copper oxide, Y includes a hydroxamic acid group, a thiol group, a monophosphate group, a phosphonate or phosphonic acid group, a triazolyl group, a thiazolyl group, a benzimidazolyl group, or a pyridinyl group. For silicon oxide or glass, Y is a silyl group. For gold, copper, and silver, Y is a thiol group (—SH) or a disulfide group (—S—S—). For platinum, preferably Y includes a pyridinyl or a phosphine group.

The AFM bound to the substrate may be represented as follows:

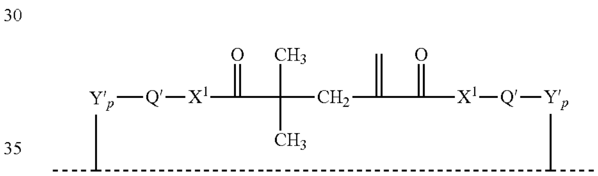

where the dashed line represents the surface of a substrate, and the bond between the substrate and binding group Y' may be a covalent or ionic bond as described supra. The remaining groups are as previously described for the surface-modified filler particles. As can be seem, such surface functionalized substrates the provide an α,β-ethylenically unsaturated group that may be copolymerized with various monomers or polymerizable compositions. In particular, the AFM surface modified substrate may be subsequently coated with the polymerizable composition containing the AFM. It is believed that the ethylenically unsaturated group will be incorporated into the polymerizable composition during curing providing a secure bond between substrate and coating.

The addition fragmentation agents are also useful in preparing dental compositions as described in US 2016/0008234 (Joly et al.), incorporated by reference in its' entirety.

EXAMPLES

As used herein, all parts and percentages are by weight unless otherwise specified. The addition fragmentation agent is referred to in the examples as an addition fragmentation ligand (AFL). All commercial materials were used as obtained from the vendor.

Test Methods

Diametral Tensile Strength (DTS) Test Method

Diametral tensile strength of a cured composition was measured in this test. An uncured test sample composition was injected into a 4-mm (inside diameter) glass tube and the tube was capped with silicone rubber plugs. The tube was compressed axially at approximately 2.88 kg/cm$^2$ pressure for 5 minutes. The sample was then light cured for 80 seconds by exposure to a XL 1500 dental curing light (3M ESPE, St. Paul, Minn.), followed by irradiation for 90 seconds in a Kulzer UniXS curing box (Heraeus Kulzer GmbH, Germany). The test sample was cut with a diamond saw to form disks about 2 mm thick, which were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Test results were reported in MPa (megapascals) as the average of multiple measurements.

Stress Test Method (Cusp Deflection)

The Stress Test Method measures the stress development during the curing process of a test sample composition. An 8×2.5×2 mm slot was machined in a rectangular 15×8×8 mm aluminum block to form a test fixture for each test sample. The slot was located 2 mm along an edge, thus forming a 2 mm wide aluminum cusp adjacent to and parallel to the 2 mm wide cavity containing compositions to be tested. A linear variable displacement transducer (Model GT 1000, used with an E309 analog amplifier, both from RDP Electronics, United Kingdom) was positioned so as to measure the displacement of the cusp tip as the composition photocured at room temperature. Prior to testing, the slot in the aluminum block was sandblasted using Rocatec Plus Special Surface Coating Blasting Material (3M ESPE, St. Paul, Minn.), treated with RelyX Ceramic Primer (3M ESPE), and finally treated with a dental adhesive, Adper Easy Bond (3M ESPE). The slot was fully packed with approximately 100 mg of the sample compositions. The material was irradiated for 1 minute with a dental curing lamp (Elipar S-10, 3M ESPE) positioned almost in contact (<1 mm) with the material in the slot, then the displacement of the cusp in microns was recorded 9 minutes after the lamp was extinguished.

Overlap Shear Test

The overlap shear strength was tested using aluminum test coupons measuring 1×4×1/16 inch (2.54×10.2×0.159 cm). Approximately 2.54 cm of the bonding surface of the coupon was abraded with an abrasive pad (Scotch-Brite Heavy Duty Scour Pad, 3M Company; St. Paul, Minn., USA). The coupon was then cleaned by squirting methyl ethyl ketone (MEK) on the coupon on a paper towel and wiping off the MEK with paper towels. Three coupons were prepared for each test adhesive sample.

An adhesive test sample was prepared by mixing the adhesive composition and dispensing 4 lines of adhesive onto the abraded area such that the adhesive covers a 2.54×1.27 cm area. Spacer beads (3-5 mil (0.0762-0.127 mm) diameter beads (Class VI Soda Lime Glass Sphere beads, MO-SCI Specialty Products; Rolla, Mo., USA) were sprinkled over the adhesive surface. A second coupon was placed over the adhesive such that the adhesive overlap was 2.54 cm×1.27 cm×0.127 mm, and the free ends of the coupons extend in opposite direction. A binder clip was placed over the overlapping portions of the coupons and a second binder clip was placed on the other end of the coupons. The adhesive test sample was allowed to cure 5-7 days at room temperature.

The test was conducted on a tensile testing device with a 5625 lb load cell at a rate of 0.1 inch per minute. The force at failure was recorded in pounds per square inch and reported in megapascals (MPa). Tensile testing devices are available under the trade designations Insight 30 MTS or Sintech 5/GL, from MTS Systems Corporation, Eden Prairie, Minn., USA.

Adhesive Handling Test

The handling of an adhesive composition is evaluated by the wet out of the adhesive on a substrate, and the work life, i.e., how long an adhesive can be worked before gelling and curing. An adhesive test sample was prepared by dispensing 12 dots of (approximately 1.8 cm in diameter) of the adhesive in a row on an 8×2 inch (20.3×5.08 cm) high density polyethylene (HDPE) test coupon. Spacer beads (see Overlap Shear Test) were sprinkled onto the entire adhesive surface of each dot and glass microscope slide coverslips were pressed down over the first 2 dots while a stopwatch was started. After 5 minutes, coverslips were pressed onto the next to dots. This process was continued until all of the dots were covered. The wet out time is reported in minutes as last the time in which the adhesive wets the coverslip sufficiently to create a bond, e.g., if the adhesive wets to the edges of the coverslip at 10 minutes, but not at 15, the wet out time is reported as 10 minutes.

The "work life" of each adhesive was evaluated by gently twisting the coverslip with a wooden applicator stick at one minute intervals starting with the first 2 dots. The Work Life is reported as the time when the coverslip can no longer be moved by the stick.

Adhesive Curing Stress Test

The curing stress that a structural adhesive undergoes during polymerization was evaluated by measuring the deformation of the adhesive on an aluminum shim after curing. A greater curl measurement indicates greater stress in the cured adhesive. The testing procedure and apparatus are described in U.S. patent application Ser. No. 13/169,306, filed Feb. 11, 2012.

Materials

- 1,2-epoxy-3-phenoxypropane—TCI America, Portland, Oreg., USA
- 1-methoxy-2-propanol—Alfa Aesar or JT Bauer
- 2-hydroxyethylmethacrylate (HEMA)—Alfa Aesar or JT Bauer
- 2-mercaptoethanol—Alfa Aesar, Ward Hill, Mass., USA
- 3-chloro-2-chloromethyl-1-propene—Secant Chemicals, Inc., USA
- 3-isocyanatopropyltriethoxysilane—Sigma Aldrich, St. Louis, Mo., USA
- 3-triethoxysilylpropyl isocyanate—Alfa Aesar, Ward Hill, Mass., USA
- BHT—butylated hydroxytoluene, Sigma-Aldrich, Milwaukee, Wis., USA
- Cobalt(II) acetate tetrahydrate—Alfa Aesar, Ward Hill, Mass., USA
- CPQ—camphorquinone, Sigma-Alrich
- DDDMA—dodecanedioldimethacrylate, Sartomer
- Dibutyltin dilaurate—Alfa Aesar, Ward Hill, Mass., USA
- Dimethyl glyoxime—Alfa Aesar, Ward Hill, Mass., USA
- DI water—deionized water
- Diol 2—diol prepared as described in U.S. Patent Publication No. 2012/0208965 under Example 2—Preparation of AFM-2 via Diol 2.
- DPIHFP—Diphenyliodonium hexafluorophosphate (>98%), Sigma-Aldrich
- DP807 adhesive—2-part curable acrylic resin; 3M Scotch-Weld™ Acrylic Adhesive
- Resin DP807 Duo-pak, 3M Company; St. Paul, Minn.
- ENMAP—ethyl N-methyl-N-phenyl-3-aminopropionate, CAS No. 2003-76-1; this is the compound of Formula 1-a in U.S. Pat. Appl. No. 2010-0311858 (Holmes) The compound may be synthesized by the methods described by Adamson, et al., JCSOA9; J. Chem. Soc.; 1949; spl.144,152, which is incorporated herein by reference.

ERGP-IEM—prepared as described in the Example section of EP Patent Publication Number EP 2401998

Ethanol—Pharmaco-AAPER, Brookfield, Conn., USA

Ethyl acetate—EMD Chemicals Inc., Gibbstown, N.J., USA

GF-31 Silane—3-Methacryloxypropyltrimethoxysilane, Wacker Chemie AG, Munich,

Germany; Silquest A-174, Momentive Performance Materials Albany, N.Y., also used Irgacure™ 651 photoinitiator obtained from Ciba Specialty Chemicals.

Nalco 2327k silica sol—20 nanometer average particle size silica particles in an aqueous sol, 41 wt. % solids, Nalco Company; Naperville, Ill.

—$NH_4OH$ solution—Ammonium hydroxide solution, 30% $NH_4OH$ in water—Sigma Aldrich Nanozirconia filler—silane-treated nanozirconia powder was prepared as described in U.S. Pat. No. 7,156,911, Preparatory Example 1A except that GF-31silane was used instead of SILQUEST A-1230. The GF-31silane was charged at approximately 1.2 millimole silane/g oxide.

Nanosilica filler (also referred to as 20 nm silica)—silane-treated nanosilica powder, with a nominal particle size of 20 nm; prepared as described in U.S. Pat. No. 6,572,693 (column 21, lines 63-67 for nanosized particle filler, Type #2)

Particle A (125 $m^2/g$ silica/zirconia nanocluster)—aggregated particle cluster material prepared as described generally in U.S. Pat. No. 6,730,156, Preparatory Example A. The material had a surface area of 125 $m^2/g$, and a weight ratio of silica/zirconia of 73/27. Preparation of the material is more specifically described in U.S. Patent application No. 20110196062, Fillers and Composite Materials with Zirconia and Silica Nanoparticles, (Bradley) paragraphs [0067]-[0073], filed Oct. 9, 2009, and references therein (namely, U.S. Pat. No. 6,376,590 (Kolb, et al.), filed on Oct. 28, 1999, or U.S. Pat. No. 7,429,422 (Davidson et al.), filed Jun. 7, 2007,) each of which is hereby incorporated by reference.

PET film—5 mil thick polyester film prepared as described in Example 29 of U.S. Pat. No. 6,893,731 (Kausch)

Pentaerythritol triacrylate was obtained from Sartomer USA, LLC; Exton, Pa.

Prostab 5198—4-hydroxy-TEMPO, Sigma Aldrich; St. Louis, Mo. USA

Pyridine—Alfa Aesar, Heysham, Lanc, England

Sodium metal—Alfa Aesar, Ward Hill, Mass., USA

UDMA—Rohamere™ 6661-0 (diurethane dimethacrylate, CAS No. 41 137-60-4), Rohm Tech, Inc., Malden, Mass.

Vazo™ 67—free radical initiator, DuPont, Wilmington, Del.

$YbF_3$—Ytterbium fluoride, 100 nanometer particle size; Sukgyung, Korea

Instrumentation: Proton nuclear magnetic resonance ($^1H$ NMR) spectra and carbon nuclear magnetic resonance ($^{13}C$ NMR) spectra were recorded on a 500 MHz spectrometer.

Preparatory Example

Diol 1

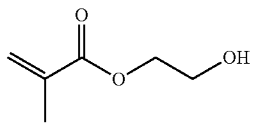

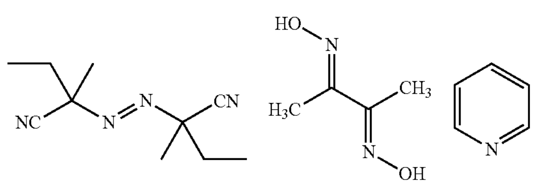

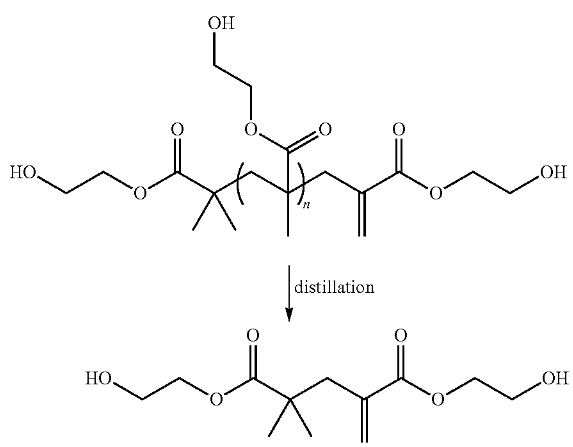

An oven-dried, three-neck 250 mL round-bottomed flask was equipped with a magnetic stir bar, gas inlet adapter, and 250 mL pressure-equalizing addition funnel capped with a rubber septum, and a rubber septum. The apparatus was allowed to cool to room temperature under nitrogen. HEMA (100 mL, 107.3 g, 824.5 mmol) and Vazo™ 67 (0.215 g, 1.12 mmol) were added to the reaction flask and the mixture was stirred. The addition funnel was charged with HEMA (200 mL, 214.6 g, 1649 mmol), and Vazo™ 67 (0.430 g, 2.24 mmol). The solutions of Vazo™ 67 in HEMA were spared with nitrogen for 30 minutes after which the reaction was maintained under nitrogen. Then cobalt(II) acetate tetrahydrate (0.104 g, 0.418 mmol), dimethyl glyoxime (0.158 g, 1.36), and pyridine (0.250 mL, 0.245 g, 3.10 mmol) were added to the pot and stirred while heating to 75° C. in an oil bath. The solution of HEMA and Vazo™ 67 were added to the pot dropwise over 1.5 hours. After an additional hour, Vazo™ 67 (0.0164 g, 0.0853 mmol) was added to the pot. The reaction was allowed to stir at 75° C. for an additional 18 hours and then allowed to cool to room temperature. The dimer product was distilled from the reaction mixture using a short-path distillation apparatus. The dimer distilled at approximately 140° C. at a pressure of 0.09 mm Hg. A colorless, clear viscous liquid was obtained (136.2 g). 50 g of the distilled product was dissolved in ethyl acetate (250 mL) and washed with deionized water (3×125 mL). The ethyl acetate solution was dried over sodium sulfate for 30 minutes and then vacuum filtered to remove the drying agent. The ethyl acetate solution was concentrated in vacuo to provide Diol 1 (26.13 g).

Example 1

AFL-1

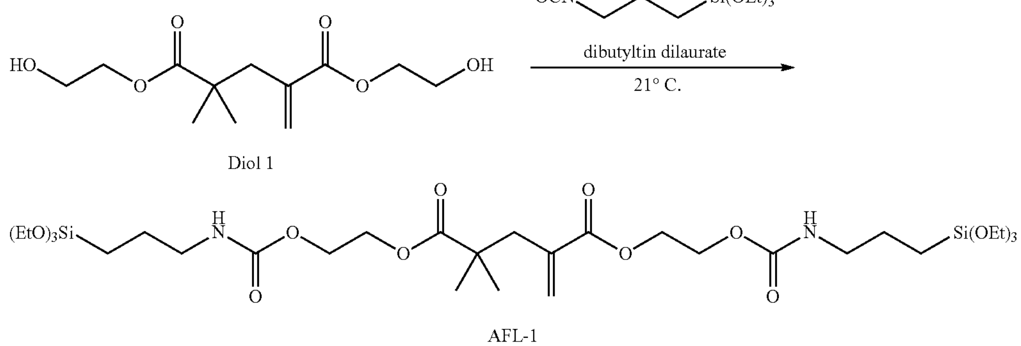

A 40 mL amber bottle was charged with Diol 1 (7.500 g, 28.82 mmol) and 3-isocyanatopropyl triethoxysilane (14.255 g, 57.63 mmol). A magnetic stir bar was added to the bottle. With stirring, dibutyltin dilaurate (2 drops from the tip of a glass pipette) was added and the reaction was sealed with a Teflon-lined plastic cap. After 3 days, the reaction was sampled, and $^{1}H$ NMR analysis was consistent with the desired product, AFL-1. AFL-1 (21.73 g, 28.79 mmol, 99.9%) was obtained as a colorless, clear viscous material.

Example 2

AFL-2

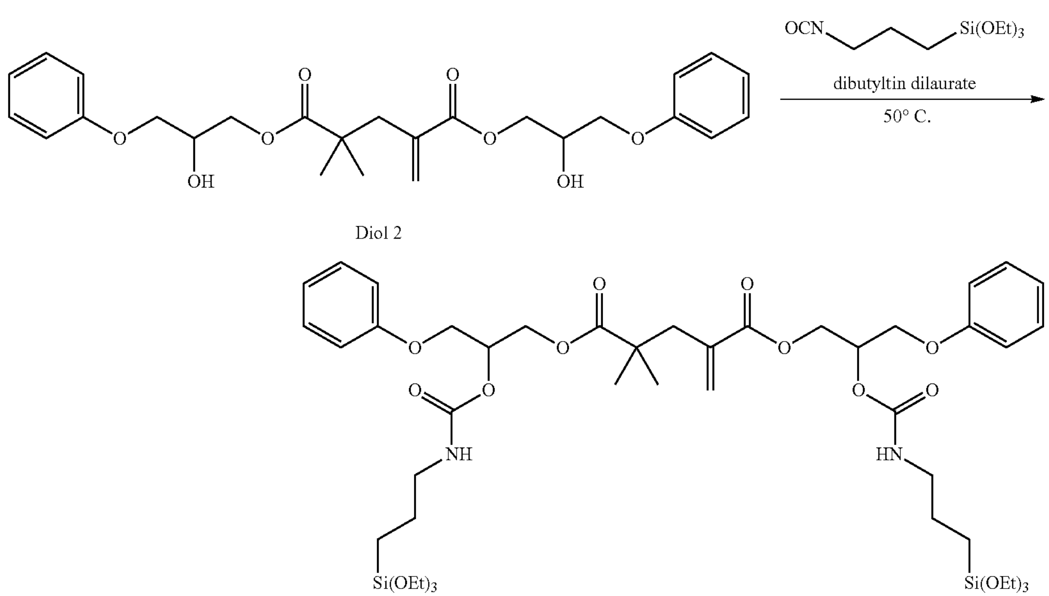

A 40 mL amber bottle was charged with Diol 2 (10.00 g, 21.16 mmol) and 3-isocyanatopropyl triethoxysilane (10.47 g, 42.33 mmol). A magnetic stir bar was added to the bottle. With stirring, dibutyltin dilaurate (2 drops from the tip of a glass pipette) was added and the reaction was sealed with a Teflon-lined plastic cap. The reaction mixture was heated to 50° C. with stirring. After 2 days, the reaction was cooled to room temperature and sampled. $^1$H NMR analysis was consistent with the desired product, AFL-2. AFL-2 (20.33 g, 21.02 mmol, 99.3%) was obtained as a very pale yellow, clear viscous material.

Example 3

AFL-3

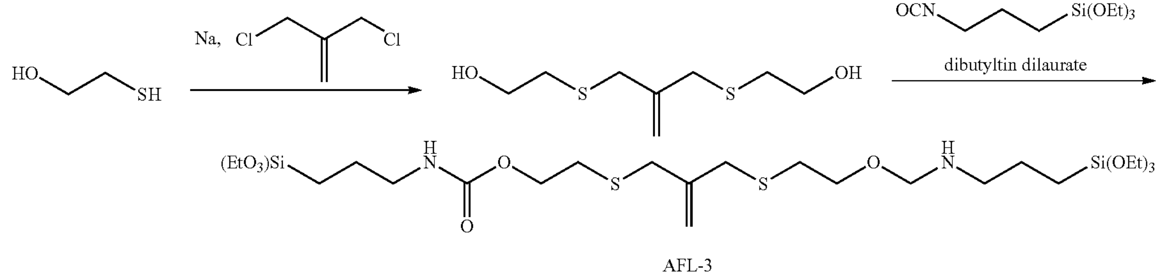

A solution was prepared by dissolving 2-mercaptoethanol (25.60 g, 0.328 mol) in 100 mL of ethanol in a 500 mL 2-neck round-bottom flask equipped with a magnetic stirring bar, condenser and a dropping funnel. With vigorous stirring, sodium metal (8.20 g, 0.356 mol) was added in small pieces slowly to control the exotherm during addition. After complete addition of the sodium metal, the mixture was stirred under a nitrogen blanket until the flask contents cooled to room temperature. A solution of 3-chloro-2-chloromethyl-1-propene ((20 g, 0.16 mol) in 50 mL of ethanol) was added dropwise using the dropping funnel to form a white cloudy mixture then a heterogeneous mixture with a white solid after all of the dichloro propene component was added. The flask contents were refluxed for 45 minutes then cooled to room temperature. The white solid was removed by vacuum filtration and the filter cake was washed with excess ethanol on top of the original filtrate. The solvent was removed in a rotary evaporator followed by drying in a vacuum pump to provide a colorless liquid. The crude product was distilled under vacuum (6-7 torr) and 135-150 C to provide the desired product, 2-methylenepropane-1,3-bis(2-hydroxyethyl sulfide, with 75-80% recovery.

A mixture was prepared by charging 2-methylenepropane-1,3-bis(2-hydroxyethyl sulfide) (7.0 g, 0.034 mol), 3-triethoxysilylpropyl isocyanate (16.60 g, 0.067 mol), BHT (0.016 g) and dibutyltin dilaurate catalyst (3 drops) into a 100 mL glass jar. The jar was swirled by hand for two minutes during which the mixture started to blend and react. The mixture became clear in color with some exotherm. The jar was left to cool to room temperature. IR spectrum showed complete disappearance of the NCO band (2200-2400 cm-1). NMR was recorded and found to be consistent with the desired structure of AFL-3. The reaction yield was quantitative.

Examples 4-5, Control Example C1

Functionalized Fillers

In Example 4, a functionalized filler was prepared by mixing 10 g of Particle A, 1.0502 g of AFL-1, 10.64 g of ethyl acetate, and 0.21 g of a $NH_4OH$ solution, and stirring overnight at room temperature. Then the mixture was flash dried and then dried in an oven for 30 minutes at 80° C.

In Example 5, a functionalized filler was prepared as in Example 4 except that the composition was 10 grams of Particle A, 1.055 g of AFL-3, 0.944 g GF-31 silane, 10.473 g of ethyl acetate and 0.203 g of $NH_4OH$ solution.

Control Example C1 was prepared as in Example 4 except that the composition was 10 g of Particle A, 2.0999 g of GF-31 silane, 20.5632 g of ethyl acetate, and 0.4002 g of NH4OH solution.

Examples 6-7, Control Example C2

Resins

A resin composition was prepared by hand mixing the composition shown in Table 1 to form a uniform mixture.

TABLE 1

Resin Composition

| Component | Weight - grams |
|---|---|
| UDMA Resin | 2.1508 |
| CPQ | 0.0644 |
| DPIHFP | 0.0603 |
| ENMAP | 0.3028 |
| BHT | 0.0304 |
| DDDMA | 0.586 |
| ERGP-IEM | 16.9098 |

In Example 6, a paste suitable for dental resins was prepared by mixing 2.675 g of the resin mixture, 0.5493 g of $YbF_3$, 0.2855 g of Nanosilica filler, 0.1536 g of Nanozirconia filler, 0.0669 g of the filler from Example 4, and 6.2269 g of the filler from Example C1 with a speed mixer.

Example 7 was prepared as in Example 6 except the composition was 2.675 g of resin, 0.5497 g of YbF3, 0.2862 g of Nanosilica filler, 0.1539 g of nanozirconia filler, and 6.3361 g of the filler from Example 5.

Control Example C2 was prepared as in Example 7 except that the filler from Example C1 was used.

The adhesives were tested for diametral strength (DTS) and stress (Cusp Deflection) according to the above test methods. Results are shown in Table 2.

TABLE 2

| Example | A-174 or GF-31 Silane (Wt %) | AFL Ex 4 (Wt %) | AFL Ex 5 (Wt %) | DTS (MPa) | Cusp Deflection (micrometers) |
|---|---|---|---|---|---|
| 6 | 90 | 10 | 0 | 82.32 | 3.13 |
| 7 | 90 | 0 | 10 | 80.73 | 2.54 |
| C2 | 100 | 0 | 0 | 85.08 | 3.31 |

Examples 8-12 and Control Example C3

Preparation of Functionalized Nanoparticles

Compositions were prepared having the components shown Table 2 according to the following procedure. Nalco 2327k silica sol was added to an 8 ounce (235 mL) glass bottle with Teflon-wrapped threads and stirred with a magnetic stir bar. Solutions were prepared by mixing methoxypropanol, Prostab, silane (3-methactyloxy propyl trimethoxysilane), and AFL-1 or AFL-2 prepared as described in Examples I and 2, respectively, in a 4 ounce (115 mL) amber glass bottle. The solution was then slowly added to the silica sol in the 8 ounce bottle with stirring over approximately 5 minutes.

The glass bottle was then sealed with a Teflon-lined metal cap, Teflon tape, and electrical tape. The reaction was heated to 90° C. with stirring. After approximately 18 hours, the reaction mixture was transferred to a 250 mL round-bottomed flask and concentrated to approximately 45 wt % solids in vacuo (approximately half the original volume). Approximately 55 grams of methoxypropanol was added to lower the solids back to approximately 20 wt %. The solution was then concentrated again to approximately 45 wt % functionalized nanoparticle solids (about 50 mL) in vacuo.

Control Example C3 was prepared according to the same procedure except that no AFL was used and after concentrating to about 45 wt % solids, approximately 110 grams of methoxy propanol was added to dilute to about 20% solids and then concentrated again to about 45 wt %.

The wt % solids of each example were determined by adding approximately 0.250 g of the final solution to an aluminum pan and drying in an oven set at 125° C. for 45 minutes. The sample was then removed from the oven, allowed to cool to room temperature, and the mass of the dried sample was measured and used to calculate percent solids in the nanoparticle solution. The functionalized nanoparticle compositions are suitable as fillers in resin compositions.

TABLE 2

| Component | Nanoparticle compositions - grams C3 | Ex 8 | Ex 9 | Ex 10 | Ex 11 | Ex 12 |
|---|---|---|---|---|---|---|
| Silica sol | 100 | 50 | 50 | 50 | 50 | 50 |
| Methoxy propanol | 112.5 | 56.25 | 56.25 | 56.25 | 56.25 | 56.25 |
| Silane | 6.36 | 1.909 | 1.273 | 2.546 | 1.909 | 1.273 |
| AFL-1 | 0 | 1.935 | 2.902 | 0 | 0 | 0 |
| AFL-2 | 0 | 0 | 0 | 1.239 | 2.478 | 3.718 |
| Prostab - 0.05 wt % solution in water | 0.025 | 0.0125 | 0.0125 | 0.0125 | 0.0125 | 0.0125 |
| Final wt % solids | 47.4 | 48.7 | 46.9 | 43.4 | 45.8 | 46.2 |

Examples 13-17, Control Example C4

Hardcoats

Hardcoat solutions were prepared by combining the methoxy propanol solutions of functionalized silica nanoparticles from Examples 8-13 and C3 with pentaerythritol triacrylate and Irgacure™ 651 in the amounts shown in Table 3 in a 20 mL glass vial. Additional methoxy propanol was added to bring the weight percent solids of the solution to 50 percent. The solutions were mixed well and sonicated for 2-5 minutes.

TABLE 3

| Nanoparticle Composition | Hardcoat Compositions - grams Ex C4 | Ex 13 | Ex 14 | Ex C2* | Ex 15 | Ex 16 | Ex 17 |
|---|---|---|---|---|---|---|---|
| Ex C3 | 5.274 | | | 5.274 | | | |
| Ex 8 | | 5.134 | | | | | |
| Ex 9 | | | 5.327 | | | | |
| Ex 10 | | | | | 5.766 | | |
| Ex 11 | | | | | | 5.463 | |
| Ex 12 | | | | | | | 5.416 |
| Pentaerythritol Triacrylate | 2.45 | 2.45 | 2.45 | 2.450 | 2.450 | 2.450 | 2.450 |
| Irgacure ™ 651 | 0.05 | 0.05 | 0.05 | 0.050 | 0.050 | 0.050 | 0.050 |
| Methoxy Propanol | 2.226 | 2.366 | 2.173 | 2.226 | 1.734 | 2.037 | 2.084 |

The solutions were coated onto 6×14 inch sheets of PET film using a #12 wire-wound rod (RD Specialties, Webster, N.Y.). The coated samples were dried in an oven set at 75° C. for 30 minutes. The coated films were then cured by irradiating with UV light (850 mJ/cm$^2$, UVB) using a UV processor (Fusion UV System, Inc., Gaithersburg, Md.) equipped with an H-bulb and operated under nitrogen atmosphere at a line speed of 24 feet/min (2 passes) to provide hardcoats on the PET film.

After irradiation, the coated films were measured for film curl, hardcoat thickness, and pencil hardness. Results are shown in Table 4. The film curl was measured on a 7.6×7.6 cm square sample that was cut from the center of the coated film. The sample was placed on a flat surface, and the height of each corner was measured using a ruler. The total curl was the sum of the height at the four corners.

The film thickness was measured at each corner of the 7.6×7.6 cm square and in the middle of each side (eight measurements total) using a dial gage (Mitutoyo Digital Dial Gauge, Model ID-F125E, Mitutoyo Corp.; Aurora, Ill.). The average film thickness was calculated using these eight measurements.

The pencil hardness was measured on each hardcoat using an Elcometer 3086 motorized pencil hardness tester (obtained from Elcometer Inc. of Rochester Hills, Mich.) with a 7.5 N load following ASTM D3363.

Test results are shown in Table 4.

TABLE 4

| | Hardcoat Properties Example Ex C4[a] | Ex 13 | Ex 14 | Ex C4[b] | Ex 15 | Ex 16 | Ex 17 |
|---|---|---|---|---|---|---|---|
| | Film Curl Measurements | | | | | | |
| Corner height measurements (mm) | 12.0 | 12.0 | 9.0 | 11.0 | 11.0 | 8.5 | 4.0 |
| | 12.5 | 1.0 | 2.0 | 11.0 | 2.0 | 1.0 | 0.5 |
| | 3.5 | 13.0 | 9.0 | 2.0 | 1.5 | 7.0 | 1.0 |
| | 1.5 | 1.0 | 2.0 | 2.0 | 10.0 | 2.0 | 3.0 |
| Total Corner height (mm) | 29.5 | 27.0 | 22.0 | 26.0 | 24.5 | 18.5 | 8.5 |
| % to Control | 100 | 91.5 | 74.6 | 100 | 94.2 | 71.2 | 32.7 |

TABLE 4-continued

| | Hardcoat Properties Example | | | | | | |
|---|---|---|---|---|---|---|---|
| | Ex C4[a] | Ex 13 | Ex 14 | Ex C4[b] | Ex 15 | Ex 16 | Ex 17 |
| | Hardcoat Thickness | | | | | | |
| Corner & side | 10 | 11 | 10 | 10.0 | 10.0 | 10.0 | 10.0 |
| measurements | 10 | 11 | 11 | 10.0 | 10.0 | 10.0 | 10.0 |
| (μm) | 9 | 10 | 11 | 9.0 | 10.0 | 10.0 | 10.0 |
| | 11 | 11 | 11 | 10.0 | 10.0 | 11.0 | 10.0 |
| | 10 | 11 | 10 | 10.0 | 10.0 | 10.0 | 9.0 |
| | 10 | 11 | 11 | 9.0 | 9.0 | 11.0 | 9.0 |
| | 10 | 11 | 11 | 9.0 | 10.0 | 10.0 | 10.0 |
| | 11 | 11 | 11 | 10.0 | 10.0 | 9.0 | 10.0 |
| Avg (μm) | 10.1 | 10.9 | 10.8 | 9.6 | 9.9 | 10.1 | 9.8 |
| Std Deviation | 0.6 | 0.4 | 0.5 | 0.5 | 0.4 | 0.6 | 0.5 |
| Relative to Control (%) | 100 | 107.4 | 106.2 | 100 | 102.6 | 105.2 | 101.3 |
| | Hardness | | | | | | |
| Pencil hardness | 3H | 3H | 3H | 3H | 3H | 3H | 3H |

Control C4[a] was prepared and tested with Examples 13-14, and Control C4[b] was prepared and tested with Examples 15-17

Examples 18-21, Control Example C7

AFL Modified Structural Adhesives

A 2-part methyl methacrylate structural adhesive (DP807) was modified with AFL-1 from Example 1 in the amounts shown in Table 6. The DP807 adhesive was supplied in a duo-pak cartridge with a base part and an accelerator part, to be dispensed and mixed in a 1:1 ratio from the cartridge.

Each part was removed from the cartridge and separately mixed with the same amount of AFL-1 shown in Table 10, e. g, 0.41%. After mixing, each part was charged back into its respective container in the cartridge. The adhesive was mixed and dispensed from the cartridge in a 1:1 ratio so the total percentage of AFM remained the same, e.g., 0.41%.

The structural adhesives were tested for Overlap Shear Strength, Handling Properties (wet-out and work life), and Curing Stress according to test procedures described above. Test results are shown in Table 5. The results for overlap shear strength show an acceptable strength for all of the adhesives with increased wet out and work life times for the examples containing AFL-1. The addition of AFL-1 to the adhesive formulation also showed a significant decrease in stress during curing as indicated by a drop in the measured aluminum shim height at 2.125" width with a corresponding decrease in the shim curl.

TABLE 5

| | Example | | | | |
|---|---|---|---|---|---|
| | Ex C5 | Ex 18 | Ex 19 | Ex 20 | Ex 21 |
| | Structural Adhesive Compositions - weight % | | | | |
| DP807 | 100 | 99.59 | 99.18 | 98.35 | 95.88 |
| AFM-1 | 0 | 0.41 | 0.82 | 1.65 | 4.12 |
| | Overlap Shear Strength* - psi | | | | |
| Sample 1 | 3611 | 3875 | 3669 | 3435 | 3450 |
| Sample 2 | 3420 | 3491 | 3660 | 3088 | 3150 |
| Sample 3 | 3894 | 3389 | 3536 | 2798 | 3255 |
| Mean | 3642 | 3585 | 3622 | 3107 | 3285 |
| SD | 238 | 256 | 74 | 319 | 152 |

TABLE 5-continued

| | Example | | | | |
|---|---|---|---|---|---|
| | Ex C5 | Ex 18 | Ex 19 | Ex 20 | Ex 21 |
| | Handling Properties - minutes | | | | |
| Wet Out (min) | 5 | 5 | 5 | 10 | 15 |
| Work Life (min) | 6.5 | 9 | 11 | 14.5 | 20.5 |
| | Curing Stress Test Shim Height at 2.125 inches width | | | | |
| N | 4 | 4 | 4 | 4 | 4 |
| Mean - um | 1587.32 | 1585.52 | 1519.68 | 1306.60 | 863.78 |
| Std Dev (SD) | 7.42 | 18.09 | 88.41 | 58.84 | 67.31 |
| SD as % of avg | 0.5 | 1.1 | 5.8 | 4.5 | 7.8 |
| % of control stress | 100.00 | 99.9 | 95.7 | 82.3 | 54.4 |
| Stress Reduction (%) | 0.00 | 0.1 | 4.3 | 17.7 | 45.6 |

*All samples failed cohesively. All values were acceptable (>3000 psi (20.7 megaPascals).

Examples 22-25 and Control Example C6

Structural adhesives were prepared and tested as in Examples 18-21 except that AFL-2 was used instead of AFL-1. Compositions and test results are shown in Table 6.

TABLE 5

| | Example | | | | |
|---|---|---|---|---|---|
| | Ex C6 | Ex 22 | Ex 23 | Ex 24 | Ex 25 |
| | Structural Adhesive Compositions - weight % | | | | |
| DP807 | 100 | 99.47 | 98.94 | 97.88 | 94.70 |
| AFM-1 | 0 | 0.53 | 1.06 | 2.12 | 5.30 |
| | Overlap Shear Strength* - psi | | | | |
| Sample 1 | 3611 | 3593 | 2879 | 3641 | 3273 |
| Sample 2 | 3420 | 3220 | 3155 | 3599 | 3195 |
| Sample 3 | 3894 | 3428 | 3761 | 3436 | 2824 |
| Mean | 3642 | 3414 | 3265 | 3559 | 3097 |
| SD | 238 | 187 | 451 | 108 | 240 |
| | Handling Properties - minutes | | | | |
| Wet Out (min) | 5 | 5 | 5 | 10 | 20 |
| Work Life (min) | 6.5 | 8 | 9 | 11.5 | 25.5 |
| | Curing Stress Test Shim Height at 2.125 inches width | | | | |
| N | 4 | 4 | 4 | 4 | 4 |
| Mean - um | 1444.91 | 1548.91 | 1182.37 | 1056.40 | 965.96 |
| Std Dev (SD) | 213 | 94 | 495 | 136 | 110 |
| SD as % of avg | 14.7 | 6.04 | 41.9 | 12.9 | 11.4 |
| % of control stress | 100 | 107.2 | 81.8 | 73.1 | 66.9 |
| Stress Reduction (%) | 0 | −7.2 | 18.2 | 26.9 | 33.1 |

*All samples failed cohesively. All values were acceptable (>3000 psi (20.7 megaPascals).

The invention claimed is:

1. A polymerizable composition comprising the addition-fragmentation agent comprising: 1) a labile addition-fragmentation group, and 2) at least two surface-binding functional groups, of the formula:

I

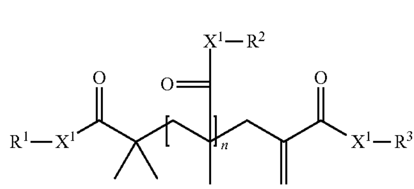

wherein $R^1$, $R^2$ and $R^3$ are each independently $Y_p$-Q'-, a (hetero) alkyl group or a (hetero)aryl group with the proviso that at least two of $R^1$, $R^2$ and $R^3$ is $Y_p$-Q'-

Q' is a covalent bond or (hetero)hydrocarbyl linking group, having a valence of p+1;

Y is a surface-binding functional group;

p is 1 or 2;

each $X^1$ is independently —O— or —$NR^4$—, where $R^4$ is H or $C_1$-$C_4$ alkyl, and n is 0 or 1;

at least one free-radically polymerizable monomer, and an initiator.

2. The polymerizable composition of claim 1 comprising:

a) 85 to 100 parts by weight of an (meth)acrylic acid ester;

b) 0 to 15 parts by weight of an acid functional ethylenically unsaturated monomer;

c) 0 to 10 parts by weight of a non-acid functional, ethylenically unsaturated polar monomer;

d) 0 to 5 parts vinyl monomer; and e) 0 to 5 parts of a multifunctional (meth)acrylate;

based on 100 parts by weight total monomer a) to e), and f) 0.1 to 12 parts by weight of the addition-fragmentation agent, based on 100 parts by weight of a) to e), and g) an initiator.

3. The polymerizable composition of claim 2 further comprising 0.01 to 5 parts of a multifunctional (meth)acrylate.

4. The polymerizable composition of claim 1, wherein at least one of $R^1$, $R^2$ and $R^3$ of the addition-fragmentation agent contain more than one $Y_p$-Q'-, where Q' is a covalent bond or a (hetero)hydrocarbyl linking group, having a valence of p+1;

p is 1 or 2; and

Y is a surface-binding functional group.

5. The polymerizable composition of claim 1 wherein Q' of the addition-fragmentation agent is selected from —O—, —S—, —$NR^4$—, —$SO_2$—, —$PO_2$—, —CO—, —OCO—, —$R^6$—, —$NR^4$—CO—$NR^4$—, $NR^4$—CO—O—, $NR^4$—CO—$NR^4$—CO—O—$R^6$—, —CO—$NR^4$—$R^6$—, —$R^6$—CO—O—$R^6$—, —O—$R^6$—, —S—$R^6$—, —$NR^4$—$R^6$—, —$SO_2$—$R^6$—, —$PO_2$—$R^6$—, —CO—$R^6$—, —OCO—$R^6$—, —$NR^4$—CO—$R^6$—, $NR^4$—$R^6$—CO—O—, and $NR^4$—CO—$NR^4$—, wherein each $R^4$ is hydrogen, a $C_1$ to $C_4$ alkyl group, or aryl group, each $R^6$ is an alkylene group having 1 to 6 carbon atoms, a 5- or 6-membered cycloalkylene group having 5 to 10 carbon atoms, or a divalent arylene group having 6 to 16 carbon atoms, with the proviso that Q-Z does not contain peroxidic linkages.

6. The polymerizable composition of claim 1 where Q' of the addition-fragmentation agent is an alkylene, of the formula —$CrH_{2r}$—, where r is 1 to 10.

7. The polymerizable composition of claim 1 where Q' of the addition-fragmentation agent is a hydroxyl-substituted alkylene.

8. The polymerizable composition of claim 1 where Q' of the addition-fragmentation agent is —$CH_2$—CH(OH)—$CH_2$—.

9. The polymerizable composition of claim 1 where Q' of the addition-fragmentation agent is an aryloxy-substituted alkylene, or an alkoxy-substituted alkylene.

10. The polymerizable composition of claim 1 wherein Y of the addition-fragmentation agent is a monophosphate, a phosphonate, a phosphonic acid, a hydroxamic acid, a carboxylic acid, and acetoacetate, an anhydride, an isonitrile group, a silyl, a disulfide, a thiol, an amino, a sulfinic acid, a sulfonic acid, a phosphine, a phenolic or a heterocyclic aromatic group.

11. polymerizable composition of claim 10 wherein Y of the addition-fragmentation agent is a silyl group of the formula: —$SiR^7 3$, wherein each $R^7$ group is independently selected from the group of alkoxy, acetoxy, and halide.

12. The polymerizable composition of claim 1, further comprising a surface-modified inorganic oxide of the formula:

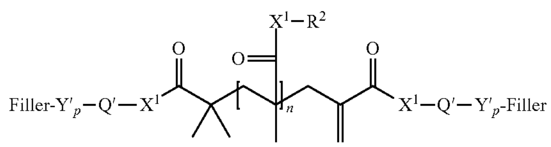

where

Filler is an inorganic filler particle, $R^2$is $Y_p$-Q'-, a (hetero)alkyl group or a (hetero)aryl group;

Q' is a covalent bond or an or a (hetero)hydrocarbyl linking group having a valence of p+1;

Y' is the residue of the surface-binding functional group Y;

p is 1 or 2;

$X^i$ is independently —O—or —$NR^4$—, where $R^4$ is H or $C_1$-$C_4$ alkyl, and n is 0 or 1.

13. A hardcoat composition comprising one or more multifunctional (meth)acrylate monomers or (meth)acrylate oligomers, and the addition-fragmentation agent comprising: 1) a labile addition-fragmentation group, and 2) at least two surface-binding functional groups, of the formula:

I

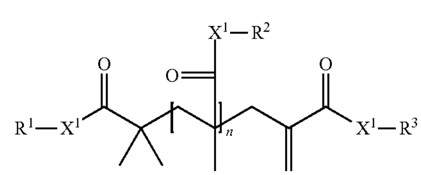

wherein $R^1$, $R^2$ and $R^3$ are each independently $Y_p$-Q'-, a (hetero) alkyl group or a (hetero)aryl group with the proviso that at least two of $R^1$, $R^2$ and $R^3$ is $Y_p$-Q'-

Q' is a covalent bond or a (hetero)hydrocarbyl linking group, having a valence of p+1;

Y is a surface-binding functional group;

p is 1 or 2;

each $X^1$ is independently —O—or —$NR^4$—, where $R^4$ is H or $C_1$-$C_4$ alkyl, and n is 0 or 1;

at least one free-radically polymerizable monomer, and an initiator.

14. A hardcoat composition comprising one or more multifunctional (meth)acrylate monomers or (meth)acrylate oli gomers, and a surface-modified inorganic oxide of the formula:

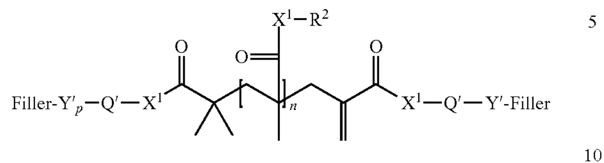

where

Filler is an inorganic filler particle, $R^2$ is $Y_p$-Q'-, a (hetero)alkyl group or a (hetero)aryl group;

Q' is a covalent bond or an or a (hetero)hydrocarbyl linking group having a valence of p+1;

Y' is the residue of the surface-binding functional group Y;

p is 1 or 2;

$X^1$ is independently —O—or—$NR^4$—, where $R^4$ is H or $C_1$-$C_4$ alkyl, and n is 0 or 1.

* * * * *